(12) United States Patent
Tizabi et al.

(10) Patent No.: US 11,541,004 B2
(45) Date of Patent: Jan. 3, 2023

(54) METHOD FOR TREATING OR MITIGATING PARKINSON'S DISEASE USING NICOTINE INHALER OR NICOTINE NASAL SPRAY

(71) Applicant: HOWARD UNIVERSITY, Washington, DC (US)

(72) Inventors: Yousef Tizabi, Silver Spring, MD (US); Robert L. Copeland, Washington, DC (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 16/897,780

(22) Filed: Jun. 10, 2020

(65) Prior Publication Data
US 2021/0386663 A1    Dec. 16, 2021

(51) Int. Cl.
*A61K 31/465*     (2006.01)
*A61K 9/00*       (2006.01)
*A61P 25/16*      (2006.01)

(52) U.S. Cl.
CPC .......... *A61K 9/0075* (2013.01); *A61K 9/0043* (2013.01); *A61K 31/465* (2013.01); *A61P 25/16* (2018.01)

(58) Field of Classification Search
CPC .. A61K 9/0075; A61K 9/0043; A61K 31/465; A61P 25/16
USPC ....................................................... 514/343
See application file for complete search history.

(56) References Cited

U.S. PATENT DOCUMENTS

| | | | |
|---|---|---|---|
| 7,387,788 B1 * | 6/2008 | Carrara | A61K 9/0014 424/449 |
| 9,655,890 B2 | 5/2017 | Hearn et al. | |
| 2008/0286340 A1 | 11/2008 | Andersson et al. | |
| 2013/0017259 A1 | 1/2013 | Azhir | |

FOREIGN PATENT DOCUMENTS

WO    WO 2019/202396 A1 * 10/2019

OTHER PUBLICATIONS

Barreto et al, Beneficial effects of nicotine, cotinine and its metabolites as potential agents for Parkinson's disease, Frontiers in Aging Neuroscience, Jan. 9, 2015, p. 1-23 (Year: 2015).*
Pfizer-1,(Pharmacia & Upjohn Co., Nicotrol® NS, Lab-0341-4.0, Jan. 2010, p. 1-20 (Year: 2010).*
Pfizer-2 (Pharmacia & Upjohn Co., Nicotrol® Inhaler, Lab-0345-4.0, Aug. 2019, p. 1-14. (Year: 2019).*
International Search Report dated Sep. 16, 2021 in International Application No. PCT/US2021/036782.
Written Opinion of the International Searching Authority dated Sep. 16, 2021 in International Application No. PCT/US2021/036782.
ClinicalTrials.gov, "Pilot Trial of Transnasal Nicotine in Parkinson Disease", U.S. National Library of Medicine, Nov. 6, 2019, retrieved on Aug. 18, 2021 from: URL: <https://clinicaltrials.gov/ct2/show/NCT03865121> ( 8 pages total).

* cited by examiner

*Primary Examiner* — Taylor V Oh
(74) *Attorney, Agent, or Firm* — Sughrue Mion, PLLC

(57) ABSTRACT

A method for treating or mitigating Parkinson's disease (PD) symptoms or progression, including administering an effective amount of nicotine to a subject in need thereof, via inhalation using a nicotine inhaler or via nasal spray using a nicotine nasal spray. Significant dose-dependent improvement of all symptoms by nicotine inhaler or nicotine nasal spray is expected. A novel treatment in PD is thus provided.

7 Claims, No Drawings

METHOD FOR TREATING OR MITIGATING PARKINSON'S DISEASE USING NICOTINE INHALER OR NICOTINE NASAL SPRAY

STATEMENT REGARDING FEDERALLY SPONSORED RESEARCH OR DEVELOPMENT

Some aspects of this invention were made in the course of Grant NIH/NIAAA R03AA022479 awarded by the National Institutes of Health and therefore the Government has certain rights in some aspects of this invention.

TECHNICAL FIELD

Methods pertain to treatment or mitigation of Parkinson's disease (PD). Particularly, methods comprise administering nicotine inhaler or nicotine nasal spray in treatment or mitigation of Parkinson's disease (PD).

BACKGROUND

Nicotine and Nicotinic Receptors

Nicotine's main targets are nicotinic receptors that are widely distributed in the central nervous system. These receptors have been directly implicated not only in reward pathway and addiction to nicotine, but also in a variety of central functions such as cognitive and attention processes, pain, mood regulation and neuronal plasticity (Campbell V C, Taylor R E, Tizabi Y. Antinociceptive effects of alcohol and nicotine: involvement of the opioid system. Brain Res. 2006, 1097(1):71-77; Tizabi Y. Nicotine and nicotinic system in hypoglutamatergic models of schizophrenia. Neurotox Res. 2007, 12(4):233-46; Tizabi Y et al. Antidepressant-like effects of nicotine and reduced nicotinic receptor binding in the Fawn-Hooded rat, an animal model of co-morbid depression and alcoholism. Prog Neuropsych Biol Psych. 2009, 33(3):398-402; Tizabi Y et al. Effects of nicotine on depressive-like behavior and hippocampal volume of female WKY rats. Prog Neuropsych Biol Psych. 2010, 34(1):62-69; Dani J A. Neuronal nicotinic acetylcholine receptor structure and function and response to nicotine. Int Rev Neurobiol. 2015; 124:3-19; Gandelman J A, Newhouse P, Taylor W D. Nicotine and networks: Potential for enhancement of mood and cognition in late-life depression. Neurosci Biobehav Rev. 2018, 84:289-298; Tizabi et al. Novel targets for parkinsonism-depression comorbidity. Prog Mol Biol Transl Sci. 2019, 167:1-24; Lewis A S and Picciotto M R. Regulation of aggressive behaviors by nicotinic acetylcholine receptors: Animal models, human genetics, and clinical studies. Neuropharmacology. 2020, 167: 107929; Terry A V Jr and Callahan P M. α7 nicotinic acetylcholine receptors as therapeutic targets in schizophrenia: Update on animal and clinical studies and strategies for the future. Neuropharmacology. 2020, 15; 170:108053). This latter effect may be directly responsible for the neuroprotective effects of nicotine (Barreto G E, Iarkov A, Moran V E. Beneficial effects of nicotine, cotinine and its metabolites as potential agents for Parkinson's disease. Front Aging Neurosci. 2015, 6:340; Tizabi Y, Getachew B. Nicotinic receptor intervention in Parkinson's disease: future directions. Cin Pharm Transl Med. 2017, 1:1-7; Tizabi Y, Getachew B, Csoka A B, Manaye K F, Copeland R L. Novel targets for parkinsonism-depression comorbidity. Prog Molec Biol Trans Sci. 2019; 167:1-24).

Nicotinic receptors (nAChRs) belong to ionotropic class of receptors. These receptors act by regulating directly the opening of a cation channel in the neuronal membrane (Dani J A. Neuronal nicotinic acetylcholine receptor structure and function and response to nicotine. Int Rev Neurobiol. 2015; 124:3-19; Papke R L, Lindstrom J M. Nicotinic acetylcholine receptors: Conventional and unconventional ligands and signaling. Neuropharmacology. 2020, 168:10802). Considerable information on interaction between these receptors and other neurotransmitter systems is now available and as indicated above therapeutic potentials for selective nicotinic receptor agonists in various neuropsychiatric and neurodegenerative disorders have been suggested. Various subtypes of these receptors with distinct anatomical, physiological, and pharmacological characteristics have been identified (see latest reviews by: Dani J A. Neuronal nicotinic acetylcholine receptor structure and function and response to nicotine. Int Rev Neurobiol. 2015; 124:3-19). The most predominant and most extensively studied subtype in the brain has a high affinity for cytisine, nicotine or acetylcholine and is formed from α4 and β2 subunits. This subtype is commonly referred to as high-affinity binding site. The other major class with a high affinity for α-bungarotoxin but low affinity for nicotine is formed from α7 subunits and can be labeled by [125I]α-bungarotoxin. This subtype is commonly referred to as low-affinity binding site. It should be noted that [125I]α-bungarotoxin also binds to neuro-muscular nicotinic receptors and in some cases to ganglionic nicotinic receptors. However, the subunit structures of the nicotinic receptors in the muscle are different from those in the ganglia, which are different from those in the CNS. Further distinction between nicotinic receptor subtypes is evident in their central distribution as well as their physiological roles. For example, [125I]α-bungarotoxin binding sites in the brain are most abundant in hippocampus and are believed to have a prominent role in neuronal growth and survival. Furthermore, these receptors appear to be involved in cognitive functions, particularly attentional processes. A role for α7 receptor subtype in central reward pathway has also been suggested. High-affinity nicotinic receptors (e.g., α4-β2 or α3 containing receptors), on the other hand, are more prominent in mesolimbic or nigro-striatal pathways and appear to be more involved in rewarding or addictive behavior, locomotor activity and antinociception or pain reduction. Both receptors appear to be involved in neuroprotection as well (Belluardo N, Mudo G, Blum M, Fuxe K. Central nicotinic receptors, neurotrophic factors and neuroprotection. Behav Brain Res. 2000, 113(1-2):21-34; Tizabi Y et al. Nicotine inhibits ethanol-induced toxicity in cultured cerebral cortical cells. Neurotoxicity Research. 2004, 6(4): 311-316; Picciotto M R and Zoli M. Neuroprotection via nAChRs: the role of nAChRs in neurodegenerative disorders such as Alzheimer's and Parkinson's disease. Front Biosci. 2008, 13:492-504; Tizabi Y, Getachew B, Csoka A B, Manaye K F, Copeland R L. Novel targets for parkinsonism-depression comorbidity. Prog Molec Biol Trans Sci. 2019; 167:1-24).

Interestingly, nicotine may also exert antidepressant-like effects that are likely mediated through high-affinity nicotinic receptors. Thus, preclinical and limited clinical studies suggest that nAChR agonists can improve depressive behavior not only in animal models but can also improve mood in depressed individuals. (Tizabi Y et al. Antidepressant-like effects of nicotine and reduced nicotinic receptor binding in the Fawn-Hooded rat, an animal model of co-morbid depression and alcoholism. Prog Neuropsych Biol Psych. 2009, 33(3):398-402; Tizabi Y et al. Effects of nicotine on depressive-like behavior and hippocampal volume of female WKY rats. Prog Neuropsych Biol Psych. 2010, 34(1):62-69; Gandelman J A, Newhouse P, Taylor W D. Nicotine and networks: Potential for enhancement of mood and cognition in late-life depression. Neurosci Biobehav Rev. 2018, 84:289-298; Tizabi Y et al. Novel targets for parkinsonism-depression comorbidity. Prog Mol Biol Transl Sci. 2019, 167:1-24).

Parkinson's Disease

Parkinson's disease (PD), the second most common progressive neurodegenerative disorder, is associated with loss of dopaminergic neurons in the substantia nigra pars compacta (SNc) that leads to striatal dopamine (DA) deficiency (Schaeffer E, et al. Pharmacological strategies for the management of levodopa-induced dyskinesia in patients with Parkinson's disease. CNS Drugs. 2014; 28: 1155-1184). This dopaminergic loss results in motor deficits characterized by akinesia, rigidity, resting tremor and postural instability as well as non-motor symptoms that might also involve other neurotransmitter systems (Perez X A. Preclinical evidence for a role of the nicotinic cholinergic system in Parkinson's disease, Neuropsychol Rev. 2015; 25:371-383). The non-motor symptoms may include: cognitive deficits (e.g., mild to severe memory impairment), emotional changes (e.g., depression, apathy and anxiety), sleep perturbations (e.g., insomnia/hypersomnia), autonomic dysfunction (e.g., bladder disturbances, orthostatic hypotension, sweating), sensory symptoms (e.g., pain, visual and olfactory deficits) and gastrointestinal symptoms (e.g., constipation, nausea) (Perez X A, 2015). The most common treatment is focused on dopamine replacement (e.g. levodopa=L-Dopa) which unfortunately losses its full efficacy in a few years and can induce severe dyskinesia. Hence more efficacious interventions without such severe side effects are urgently needed.

SUMMARY OF THE INVENTION

The present inventors have conducted an extensive research and have discovered that pulsatile stimulation of specific nicotinic receptors in selective brain regions, particularly in the nigrostriatal pathway would be critical for its therapeutic effects in PD. The present inventors have discovered that by administering nicotine via inhalation or nasal spray, it would be mimicking the smoking paradigm that has been associated with protection against PD. That is, administering nicotine via inhalation or nasal spray would be more effective in treating or mitigating PD.

In addition to its potential usefulness for improving motor dysfunctions and neuroprotection against nigrostriatal damage, nicotine inhaler or nicotine nasal spray may also be helpful in non-motor symptoms (e.g. cognitive decline and depression) that are commonly associated with neurological disorders such as PD.

DETAILED DESCRIPTION OF THE INVENTION

Role of the Nicotinic Cholinergic System in Parkinson's Disease

Multiple studies indicate that normal function of the basal ganglia is dependent on the equilibrium between the midbrain dopaminergic and striatal cholinergic systems. Thus, acetylcholine can regulate striatal DA release via an interaction at various nicotinic receptors (Perez X A, Bordia T, McIntosh J M, Quik M. α6β2* and α4β2* nicotinic receptors both regulate dopamine signaling with increased nigrostriatal damage: relevance to Parkinson's disease. Mol Pharmacol. 2010 78(5):971-80; Quik M and Wonnacott S. α6β2* and α4β2* nicotinic acetylcholine receptors as drug targets for Parkinson's disease. Pharmacol Rev. 2011, 63(4):938-66). In a number of animal models of PD (e.g. 6-OHDA lesioned rodents) the impairments in DA release appear to be exacerbated by a loss of nAChRs activation suggesting that nicotinic agonists may ameliorate the dopaminergic imbalance observed in PD and may thus be useful therapeutic targets. Indeed, a number of in-vitro and in-vivo studies in rodents and primates including genetically modified mice, have shown protective effects of nicotine against neuronal damage induced by 6-OHDA, MPTP, rotenone, paraquat, methamphetamine, glutamate and β-amyloid. These effects are mediated via selective nicotinic receptor subtypes containing β2 and α7 subunits (Quik M, Zhang D, McGregor M, Bordia T. Alpha7 nicotinic receptors as therapeutic targets for Parkinson's disease. Biochem Pharmacol. 2015, 97(4):399-407; Tizabi Y, Getachew B. Nicotinic receptor intervention in Parkinson's disease: future directions. Cin Pharm Transl Med. 2017, 1:1-7; Tizabi Y, Getachew B, Csoka A B, Manaye K F, Copeland R L. Novel targets for parkinsonism-depression comorbidity. Prog Molec Biol Trans Sci. 2019; 167:1-24).

Protective effects of nicotine against endogenous substances such as salsolinol and aminochrome that selectively damage dopaminergic cells, have also been observed (Copeland R L. Leggett Y A, Kanaan Y M, Taylor R E. Tizabi Y. Neuroprotective effects of nicotine against salsolinol-induced cytotoxicity: implications for Parkinson's disease. Neurotox Res 2005, 8(1-4):289-293; Copeland R L, Das J R, Kanaan Y M. Taylor R E, Tizabi Y. Antiapoptotic effects of nicotine in its protection against salsolinol-induced cytotoxicity. Neurotox Res. 2007, 12(1):61-69; Munoz P, Huenchuguala S, Paris I, Cuevas C, Villa M, Caviedes P, Segura-Aguilar J, Tizabi Y. Protective effects of nicotine against aminochrome-induced toxicity in substantia nigra derived cells: implications for Parkinson's disease. Neurotox Res. 2012, 22(2):177-180). Recently, the laboratory of Dr. Tizabi has provided proof of protective effects of nicotine against toxicity induced by trace elements (e.g. iron or manganese), which have also been implicated in the etiology of PD (Getachew B, Csoka A B, Aschner M, Tizabi Y. Nicotine protects against manganese and iron-induced toxicity in SH-SYSY cells: Implication for Parkinson's disease. Neurochem Int. 2019 124:19-24). Additionally, Quik et al (2015) have shown beneficial effects of nicotine against L-Dopa-induced dyskinesia in non-human primate models. Nicotine's effects are likely to involve suppression of pro-inflammatory cytokines and stimulation of neurotrophic factors (Barreto G E, Iarkov A, Moran V E. Beneficial effects of nicotine, cotinine and its metabolites as potential agents for Parkinson's disease. Front Aging Neurosci. 2015, 6:340; Perez X A, 2015; Tizabi Y et al. 2019). The majority of studies assessing the effects of nicotine have used the gum or patch to administer nicotine, which may not activate nicotinic receptors as strongly as smoking. Indeed, the very complex dynamic interaction of nicotine with its receptors, where initial stimulation can be followed by rapid and differential desensitization of receptor subtypes, has to be critically considered in experimental paradigms so that maximal outcome may be obtained (Tizabi Y and Getachew B, 2017). The present inventors have conducted an extensive research and have discovered that pulsatile stimulation of specific nicotinic receptors in selective brain regions, particularly in the nigrostriatal pathway would be critical for its therapeutic effects in PD, and thus have completed the present invention. By administering nicotine via inhalation or nasal spray, it would be mimicking the smoking paradigm that has been associated with protection against PD. Pulsatile stimulation of the central nicotinic receptors (achievable via inhalation or nasal spray) would affect the dynamic of the nicotinic receptors much more desirably than continuous nicotine administration via patch, which can result in continuous nicotinic receptor desensitization. That is, administering nicotine via inhalation or nasal spray would be more effective in treating or mitigating PD.

Motor symptoms associated with PD include tremor, freezing of gait, gait hesitation, balance, camptocormia (bent spine syndrome) and dyskinesia. In addition, there are mood, cognition, pain, sleep and gastrointestinal conditions associated with PD. Significant dose-dependent recovery of all PD symptoms as well as mood and cognitive functions are anticipated. In addition, a reduction in dyskinesia (if present) is anticipated. The present invention provides novel treatment in PD.

One example embodiment of the disclosed subject matter provides an agent for treatment or mitigation of Parkinson's disease (PD), containing nicotine as an active ingredient.

Another example embodiment of the disclosed subject matter provides a method for treating or mitigating Parkinson's disease (PD), comprising administering an effective amount of nicotine to a subject in need thereof.

In one of its aspects, the nicotine is administered via inhalation using a nicotine inhaler or via nasal spray using a nicotine nasal spray.

In one of its aspects, the nicotine is administered via inhalation using a nicotine inhaler Nicotrol®.

In one of its aspects, the nicotine is administered via nasal spray using a nicotine nasal spray Nicotrol®.

In one of its aspects, the method entails pulsatile stimulation of specific nicotinic receptors in selective brain regions.

In one of its aspect, the method is similar to nicotine intake via smoking cigarettes.

One commercially available nicotine inhaler or nicotine nasal spray is Nicotrol® by Pfizer. Nicotrol® is used to help quit smoking. This patent application is suggesting re-purposing an approved FDA medication for treatment of PD. The Nicotrol® inhaler is a cigarette-type device made up of a cartridge containing nicotine and a mouthpiece. When air is inhaled through the device, it is saturated with nicotine, which is then absorbed through the lining of the mouth and upper esophagus. The Nicotrol® nasal spray is like the product one uses for nasal congestion; one just pumps it into one's nostril and it sprays nicotine there.

The formulation of nicotine inhaler or nicotine nasal spray is per manufactured specificity of Pfizer and as approved by FDA. Similar formulation can be produced by well-known methods.

The dose of the nicotine to be used will be different depending on body weight, symptoms, treatment period, therapeutic effects, prior exposure to nicotine and the like. For example, the initial or starting dose of the nicotine via inhalation per adult might be 2 cartridges of Nicotrol®/day, which would deliver 2 mg of nicotine and will be equivalent to smoking 2 cigarette per day. Please note, each cartridge is equivalent to smoking one cigarette which delivers about 1 mg of nicotine. The dosing will be increased incrementally over days to a maximum of tolerable dose, but not exceeding 10 mg of nicotine/day.

Similarly, the dose of the nicotine via nasal spray per adult might be (0.5 mg/spray) starting with 2 bilateral puffs per day, which would be equivalent to 2 mg of nicotine intake which would be similar to smoking 2 cigarettes per day). Here also, the dosing will be increased incrementally over days to a maximum of tolerable dose, but not exceeding 10 mg of nicotine/day. Needless to say, as mentioned above, the dose to be used would vary depending on conditions specified above and the response of the patient.

Importantly, the nicotine inhaler or nicotine nasal spray may be administered in combination with other medicine (for example, well-known agents for PD treatment) for the purposes of: (1) supplementing and/or enhancing therapeutic effect of the current medication, (2) improving the kinetics and reducing or eliminating potential adverse reaction to nicotine.

Example S

The present invention is explained below in further detail with reference to Examples. However, the scope of the invention is not limited to these Examples.

Six patients received incremental doses of Nicotine Nasal Spray 10 mg/ml (0.5 mg/spray) starting with 3 bilateral puffs per day (3 mg total) for 3 days, followed by 5 bilateral puffs per day (5 mg) for 3 days, followed by 8 bilateral puffs per day (8 mg) for 4 days, followed by 10 bilateral puffs per day (10 mg) for 10 days.

Possible improvement has been reported by patients especially in impulsivity. For example, one early diagnosed PD patient has claimed that "he had connected with the drug and had a significant attenuation of his impulsive behavior." Side effects may include headache and nose irritation.

While the subject matter disclosed herein has been described in connection with what is presently considered to be practical example embodiments, it is to be understood that the present disclosure is not limited to the disclosed embodiments, and covers various modifications and equivalent arrangements included within the spirit and scope of the present invention.

What is claimed is:

1. A method for treating or mitigating Parkinson's disease (PD), comprising administering an effective amount of nicotine to a subject in need thereof,
   wherein the nicotine is administered via inhalation using a nicotine inhaler or via nasal spray using a nicotine nasal spray,
   the nicotine is administered with an initial dose of 2 mg per day, and pulsatile stimulation of specific nicotinic receptors similar to what is achieved via smoking cigarettes, but without the ill effects of tobacco smoking.

2. The method according to claim 1, wherein the nicotine is administered via inhalation using a nicotine inhaler.

3. The method according to claim 1, wherein the dosing is increased incrementally over days to a maximum of tolerable dose, but not exceeding 10 mg of nicotine/day.

4. The method according to claim 1, wherein the nicotine is administered via nasal spray using a nicotine nasal spray.

5. The method according to claim 4, wherein the nicotine is administered with an initial dose of 2 bilateral puffs per day, equivalent to 2 mg of nicotine per day.

6. The method according to claim 5, wherein the dosing is increased incrementally over days to a maximum of tolerable dose, but not exceeding 10 mg of nicotine/day.

7. The method according to claim 1, comprising pulsatile stimulation of specific nicotinic receptors in selective brain regions.

\* \* \* \* \*